(12) United States Patent
Johnson et al.

(10) Patent No.: US 8,927,876 B2
(45) Date of Patent: Jan. 6, 2015

(54) ELECTRODE ARRAY AND METHOD OF FABRICATION

(75) Inventors: Angelique Johnson, Ann Arbor, MI (US); Kensall Wise, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 254 days.

(21) Appl. No.: 13/597,970

(22) Filed: Aug. 29, 2012

(65) Prior Publication Data

US 2012/0325525 A1  Dec. 27, 2012

Related U.S. Application Data

(62) Division of application No. 12/691,924, filed on Jan. 22, 2010, now Pat. No. 8,283,569.

(51) Int. Cl.
*H05K 1/03* (2006.01)
*A61N 1/05* (2006.01)

(52) U.S. Cl.
CPC ................................. *A61N 1/0541* (2013.01)
USPC ............... 174/255; 174/391; 607/53; 607/57; 607/137; 428/458; 424/1.11; 424/422; 424/423

(58) Field of Classification Search
USPC ....................... 174/255, 391; 607/53, 57, 137; 428/458; 424/1.11, 422, 423
See application file for complete search history.

(56) References Cited

U.S. PATENT DOCUMENTS

| | | | |
|---|---|---|---|
| 4,762,135 A | 8/1988 | Van der Puije et al. |
| 5,178,957 A | 1/1993 | Kolpe et al. |
| 5,720,099 A | 2/1998 | Parker et al. |
| 5,800,500 A | 9/1998 | Spelman et al. |
| 6,374,143 B1 | 4/2002 | Berrang et al. |
| 6,782,619 B2 | 8/2004 | Corbett, III et al. |
| 6,818,911 B2 | 11/2004 | Tamamori et al. |
| 6,962,865 B2 | 11/2005 | Hanaoka et al. |
| 7,035,692 B1 | 4/2006 | Maghribi et al. |
| 7,211,103 B2 | 5/2007 | Greenberg et al. |
| 7,326,649 B2 | 2/2008 | Rodger et al. |
| 8,283,569 B2 | 10/2012 | Johnson et al. |
| 2003/0218140 A1 | 11/2003 | Tamamori et al. |

(Continued)

FOREIGN PATENT DOCUMENTS

| | | |
|---|---|---|
| EP | 2042137 A1 | 1/2009 |
| WO | 2008011721 A1 | 1/2008 |
| WO | 2011090842 A1 | 7/2011 |

OTHER PUBLICATIONS

PCT International Search Report for PCT/US2011/020741, dated Oct. 25, 2011, 5 pages.

(Continued)

*Primary Examiner* — Xiaoliang Chen
(74) *Attorney, Agent, or Firm* — Howard & Howard Attorneys PLLC

(57) ABSTRACT

An electrode array, having application as a cochlear implant, includes a tube formed of Parylene defining a hollow channel. A substrate formed primarily of Parylene is supported by the tube. In turn, a plurality of metallic electrodes and feed lines are supported by the substrate. Numerous voids are defined by the tube which opens into the hollow channel. The size and spacing of the voids regulate stiffness and curl of the tube to provide excellent fit within the cochlea.

15 Claims, 6 Drawing Sheets

(56) References Cited

U.S. PATENT DOCUMENTS

| | | | |
|---|---|---|---|
| 2003/0233133 | A1 | 12/2003 | Greenberg et al. |
| 2004/0155354 | A1 | 8/2004 | Hanaoka et al. |
| 2004/0220651 | A1* | 11/2004 | Kuzma et al. ............... 607/137 |
| 2005/0004627 | A1 | 1/2005 | Gibson et al. |
| 2005/0033377 | A1 | 2/2005 | Milojevic et al. |
| 2005/0051427 | A1 | 3/2005 | Brauker et al. |
| 2007/0007240 | A1 | 1/2007 | Wise et al. |
| 2007/0073130 | A1 | 3/2007 | Finch et al. |
| 2007/0158100 | A1 | 7/2007 | Greenberg et al. |
| 2007/0178133 | A1 | 8/2007 | Rolland |
| 2008/0027527 | A1 | 1/2008 | Kuzma et al. |
| 2009/0112288 | A1 | 4/2009 | Hur et al. |
| 2009/0143848 | A1 | 6/2009 | Greenberg et al. |
| 2009/0229739 | A1 | 9/2009 | Schuller |
| 2009/0281250 | A1 | 11/2009 | Desimone et al. |
| 2009/0311713 | A1* | 12/2009 | Pollack et al. ............... 435/6 |
| 2010/0221713 | A1* | 9/2010 | Pollack et al. ............... 435/6 |
| 2010/0233226 | A1 | 9/2010 | Ferain et al. |
| 2011/0097763 | A1* | 4/2011 | Pollack et al. ............ 435/91.2 |
| 2011/0256542 | A9* | 10/2011 | Pollack et al. ............ 435/6.12 |
| 2011/0276118 | A1* | 11/2011 | Kuzma et al. ............... 607/137 |

OTHER PUBLICATIONS

Clark et al., "A Cochlear Implant Electrode", The Journal of Laryngology and Otology, Aug. 1975, pp. 787-792.

Chen et al., "A Multichannel Neural Probe for Selective Chemical Delivery at the Cellular Level", IEEE Transactions on Biomedical Engineering, vol. 44, No. 8, Aug. 1997, pp. 760-769.

Bhatti et al., "A High-Density Electrode Array for a Cochlear Prosthesis", Transducers '03, The 12th International Conference on Solid State Sensors, Actuators and Microsystems, Boston, Jun. 8-12, 2003, pp. 1750-1753.

Wu et al., "A Curvature-Controlled 3D Micro-Electrode Array for Cochlear Implants", Transducers '05, The 13th International Conference on Solid-State Sensors, Actuators and Microsystems, Seoul, Korea, Jun. 5-9, 2005, pp. 1636-1639.

Corbett et al., "Polymer-Based Microelectrode Arrays", Mater. Res. Soc. Symp. Proc. vol. 926, 2006 Material Research Society.

Chen et al., "Design, Fabrication and Characterization of Monolithic Embedded Parylene Microchannels in Silicon Substrate", The Royal Society of Chemistry 2006, Lab Chip, 2006, 6, Mar. 30, 2006, pp. 803-810.

Johnson, "Microfabrication of Biocompatible Stimulation Electrode Arrays for Cochlear Implants", Rochester Institute of Technology, 24th Annual Microelectronic Engineering Conference, May 2006, pp. 74-79.

Bulcke et al., "Active Electrode Arrays by Chip Embedding in a Flexible Silicone Carrier", Proceedings of the 28th IEEE EMBS Annual International Conference, New York City, USA, Aug. 30-Sep. 3, 2006, pp. 2811-2815.

Wang et al., "A Parylene-Silicon Cochlear Electrode Array With Integrated Position Sensors", Proceedings of the 28th IEEE EMBS Annual International Conference, New York City, USA, Aug. 30-Sep. 3, 2006, pp. 3170-3173.

Bhatti et al., "A 32-Site 4-Channel High-Density Electrode Array for a Cochlear Prosthesis", IEEE Journal of Solid-State Circuits, vol. 41, No. 12, Dec. 2006, pp. 2965-2973.

Wang et al., "A Thin-Film Cochlear Electrode Array With Integrated Position Sensing", Journal of Microelectromechanical Systems, vol. 18, No. 2, Apr. 2009, pp. 385-395.

* cited by examiner

ELECTRODE ARRAY AND METHOD OF FABRICATION

The subject patent application is a divisional of U.S. patent application Ser. No. 12/691,924, filed on Jan. 22, 2010, which is now U.S. Pat. No. 8,283,569, the disclosure of which is hereby incorporated by reference.

STATEMENT REGARDING FEDERALLY SPONSORED RESEARCH OR DEVELOPMENT

This invention was made with government support under Grant No. EEC-9986866 awarded by the National Science Foundation. The government has certain rights in the invention.

BACKGROUND OF THE INVENTION

1. Field of the Invention

The subject invention relates to an array of electrodes. Specifically, the subject invention relates to an array of electrodes for use as part of a cochlear implant.

2. Description of the Related Art

Cochlear implants are the most widely used neural prostheses, using current stimulation to bypass the non-functional hair cells of the cochlea to directly stimulate receptor cells that drive the auditory nerve. Typical cochlear electrode arrays are fabricated with bundles of wires coated in silicone. Such wire bundles are hand assembled and are limited in the number of electrodes. A typical cochlear electrode array utilizes only 16 to 24 electrodes because of large size relative to the size of the scala tympani. The low number of electrodes results in often poor pitch specificity. The relatively large size of these electrode arrays may also cause insertion damage and limit the depth of insertion. The low insertion depth limits the pitch range provided by the implant.

The subject invention is directed toward providing an electrode array providing greater pitch specificity, greater pitch range, while resulting in minimal insertion damage.

SUMMARY OF THE INVENTION AND ADVANTAGES

The subject invention provides an electrode array. The electrode array includes a tube having at least one wall wherein the tube defines a channel. A substrate comprised of a non-conductive material is supported at least partially by the tube. The electrode includes a plurality of electrodes. Each electrode comprises a conductive material and is supported by the substrate. A plurality of feed lines comprised of a conductive material are disposed primarily within the substrate. Each feed line is electrically connected to at least one of the plurality of electrodes. At least one wall of the tube defines a plurality of voids into the hollow channel for regulating stiffness and curl of the tube.

The subject invention also provides a method of fabricating the electrode array. The method includes the step of depositing a first composition on a carrier wafer. The first composition defines a longitudinal slit and forms a first layer of the substrate. The carrier wafer is etched through the longitudinal slit to define a channel underneath the first layer. The method also includes depositing a second composition comprising a polymer through the longitudinal slit and onto the carrier wafer to form the tube around the channel and seal the longitudinal slit. The method further includes the step of disposing a plurality of feed lines comprised of conductive material on the substrate opposite the tube. The plurality of electrodes is disposed on the substrate with each electrode electrically connected to at least one of the feed lines. The method further includes the step of etching the carrier wafer opposite the substrate to define voids with each void exposing an area of the tube The areas of the tube exposed by the voids are removed to define slots within the tube. The tube and substrate are then released from the carrier wafer.

The electrode array provides a lower profile than those of the prior art, resulting in less damage when inserted into a cochlea. The electrode array also provides a greater number of electrodes and allows for deeper insertion into the cochlear, resulting in improved pitch specificity and greater pitch range. Furthermore, the slots of the tube of the electrode array assist in providing a modiolus-hugging curl to position the electrodes as close as possible to the receptor cells and reduce insertion trauma.

BRIEF DESCRIPTION OF THE DRAWINGS

Other advantages of the present invention will be readily appreciated, as the same becomes better understood by reference to the following detailed description when considered in connection with the accompanying drawings wherein.

DETAILED DESCRIPTION OF THE INVENTION

Referring to the Figures, wherein like numerals indicate like parts throughout the several views, an electrode array 20 is shown herein. The electrode array 20 is well suited for use as part of a cochlear implant (not shown), but other uses of the electrode array 20 are described further below and/or will be realized by those skilled in the art.

The electrode array 20 includes a substrate 22 at least partially supported by a tube 24. In the illustrated embodiments, the substrate 22 and tube 24 each comprise a non-conductive material. Specifically, the substrate 22 and tube 24 of the illustrated embodiments each comprise a polymer and more specifically, the substrate 22 and tube 24 each comprises poly(p-xylene), known commonly by the trade name Parylene. In the illustrated embodiments, Parylene C is utilized to form the substrate 22 and tube 24. However, in other embodiments, other types of Parylene, other types of polymers, and other types of non-conductive materials may alternatively be utilized to form the substrate 22 and tube 24. Furthermore, electrically conductive materials, such as metals, may alternatively be used to form the tube 24. Moreover, the substrate 22 and tube 24 may be formed of a combination of different materials.

The electrode array 20 may include more than one tube 24 connected to the substrate 22, i.e., a plurality of tubes 24. However, for purposes of illustrative simplicity, the electrode array 20 is shown and described herein with only a single tube 24.

Figure 16:
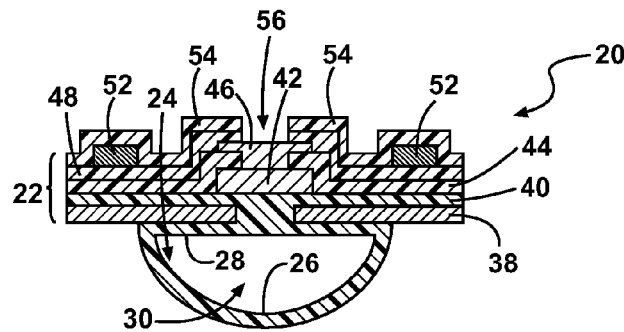
FIG. 16 is a widthwise cross sectional view of the electrode array.

The tube 24 includes at least one wall 26, 28 of defining a hollow channel 30 referred to hereafter as the tube channel 30. In the illustrated embodiment, the tube 24 has a generally semicircular cross section defined by a curved wall 26 and a generally straight wall 28, as shown in FIG. 16. The generally straight wall 28 of the illustrated embodiment is connected to the substrate 22 as described in further detail below. Other shapes for the tube 24 may be realized by those skilled in the art. Moreover, the use of the term "tube" does not necessarily imply a circular or curved shape.

In one embodiment, the at least one wall 26, 28 of the tube 24 defines a plurality of slots 32 into the tube channel 30. Specifically, in the illustrated embodiments, the slots 32 are defined by the curved wall 26. The slots 32 regulate the stiffness and curl of the tube 24. More particularly, the size of the slots 32 and spacing of the slots 32 from one another define the ability of the tube 24 to bend and curl. The slots 32 in the illustrated embodiment are generally circular or ring shaped. Of course, other shapes for the slots 32 may also be suitable. Moreover, in other embodiments (not shown), the walls 26, 28 of the tube 24 may be continuous, i.e., without any slots or other holes, to allow liquids to pass through the tube channel 30.

In the illustrated embodiment, the substrate 22 includes an interconnect region 34 and an electrode region 36. The interconnect region 34 allows for electrical connection of the electrode array 20 with at least one external device (not shown), as described further below.

The substrate 22 of the illustrated embodiment comprises a plurality of layers of Parylene. That is, several layers of Parylene are connected together to form the substrate 22. Specifically, the substrate 22 comprises a first layer 38 of Parylene, also referred to as a base layer 38. The first layer 38 is in contact with and affixed to the straight wall 28 of the tube 24.

In the illustrated embodiment, a second layer 40 of Parylene is disposed above the first layer 34. That is, the second layer 40 is disposed on the first layer 38 opposite the tube 24. The second layer 40 and the tube 24 are integrally formed as described further below. That is, the second layer 40 and tube 24 are comprised of a single unit.

The substrate 22 also supports a plurality of feed lines 42 comprised of a conductive material. The feed lines 42 of the illustrated embodiment comprise a metal. More specifically, the feed lines 42 are formed of chromium-gold-chromium (Cr—Au—Cr). In the illustrated embodiment, the pitch, i.e., the distance between a point on one feed line 42 and a corresponding point on another feed line 42, is about 10 µm. As such, a width of each feed line 42 is less than 9 µm, to maintain electrical isolation between the feed lines 42.

In the illustrated embodiment, the feed lines 42 are disposed on the second layer 40. The feed lines 42 run between the interconnect region 34 and the electrode region 36. A third layer 44 of Parylene is disposed above the feed lines 42 and the second layer 40. That is, the third layer 44 is connected to the second layer 40 opposite the tube 24. As such, the feed lines 42 are disposed primarily within the substrate 22, i.e., the feed lines 42 are encased within the substrate 22. As such, the feed lines 42 are insulated by the non-conductive material of the substrate 22. Specifically, the third layer 44 of Parylene electrically insulates the feed lines 42.

The substrate 22 also supports a plurality of electrodes 46 for conducting electrical energy. The electrodes 46 each comprise an electrically conductive material, including, but not limited to, a metal. In the illustrated embodiment, the electrodes comprise titanium-iridium (Ti—Ir). However, in other embodiments, the electrodes 46 may be formed of different metals. Furthermore, other electrically conductive material, such as conductive polymers, could be used to form the electrodes 46. Moreover, the various electrodes 46 need not be formed of the same type of material and could be formed by a combination of different materials.

In the illustrated embodiment, the electrodes 46 are supported in the electrode region 26. Particularly, the electrodes 46 are disposed above the third layer 44. At least one electrode 46 is electrically connected to at least one feed line 42. As the feed lines extend to the interconnect region 34, the feed lines 42 may electrically connect the electrodes 46 to the at least one external device. In the illustrated embodiment, each electrode 46 is electrically connected to one feed line 42.

Figure 1:
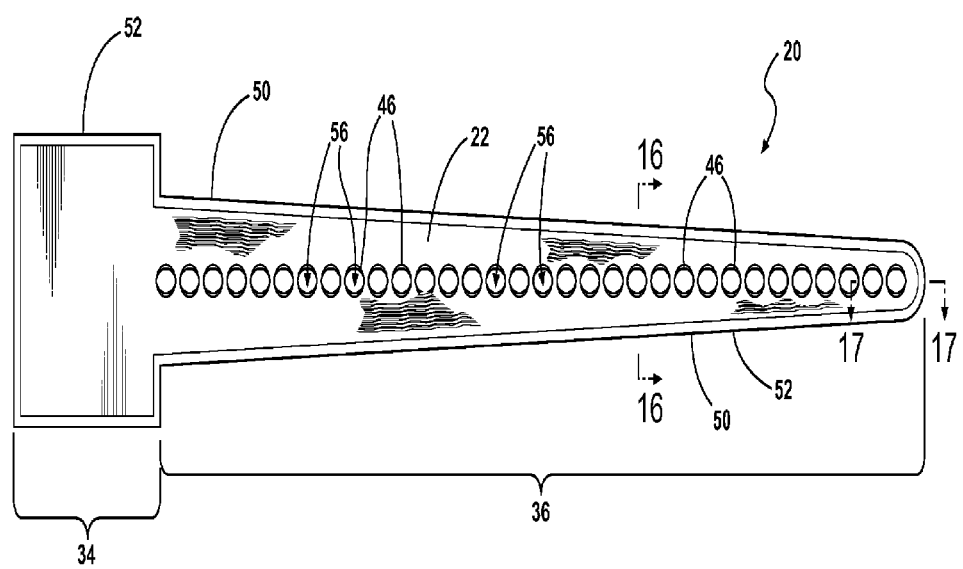
FIG. 1 is a top view of an electrode array of the subject invention showing an interconnect region and thirty-two electrode sites in an electrode region.

The electrode array 20 of the subject invention achieves a high density of electrodes 46. More specifically, the pitch between the electrodes may be less than 300 µm. In the illustrated embodiment, as shown in FIG. 1, 32 electrodes 46 are supported in the electrode region 26 having a length of about 8 mm. That is, the pitch, or center-to-center spacing, between the electrodes 46 is the illustrated embodiment is about 250 µm. By increasing the density and number of electrodes 46 the electrode array 20, when used as a cochlear implant, provides improved pitch specificity over the prior art. Of course, other number of electrodes 46 may be achieved as will be realized by those skilled in the art. During experimentation, other electrode arrays 20 (not shown) were fabricated with 64 and 128 electrodes 46.

The substrate 22 of the illustrated embodiment includes a fourth layer 48 of Parylene disposed above the third layer 44. That is, the fourth layer is supported by the third layer 44 opposite the tube 24.

The substrate 22 defines a peripheral edge 50 around its periphery. The electrode array 20 may include a curl strip 52 disposed adjacent at least a portion of the peripheral edge 50. The curl strip 52 provides rigidity to the electrode array 20 and further regulates the amount of bend and/or curl of the array 20. In the illustrated embodiment, the curl strip 52 is disposed on the fourth layer 48. A fifth layer 54 of Parylene is disposed over the curl strip 52. That is, the fifth layer 54 is disposed on the fourth layer 48 opposite the tube 24. As such, the curl strip 52 is encased within the substrate 22 around the entire peripheral edge 50.

The curl strip 52 of the illustrated embodiment is bimetallic. Specifically, the curl strip 52 is composed of Titanium-Iridium and Chromium-Gold (Ti—Ir/Cr—Au). Of course, other materials may be utilized to form the curl strip 52. Furthermore, the curl strip 52 may be formed of various independent pieces or one continuous piece.

The fourth and fifth layers 48 define a plurality of openings 56. Each opening 56 encircles at least one electrode 46 to allow electrical contact with the at least one electrode 46. Preferably, each opening 56 encircles just one electrode 46. In the illustrated embodiment, each opening 56 has a generally circular shape and a diameter less than 200 µm. However, other shapes and sizes for the openings 56 may be suitable as realized by those skilled in the art.

The electrode array 20 of the illustrated embodiment provides significantly greater flexibility than silicon-substrate devices of the prior art and are robust enough to withstand repeated flexing. Testing of the electrode array 20 results in only a 20% impedance drop after 6000 cycles of twisting the array 20 to a helical radius of about 2 mm. This testing also revealed that no shorting between the feed lines 42 and saline after the 6000 cycles of twisting.

The subject invention also provides an exemplary method of fabricating the electrode array 20. However, other methods of fabricating the electrode array 20 described above may be realized by those skilled in the art.

Figure 2:
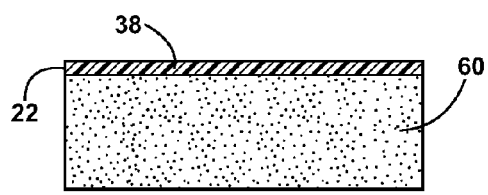
FIG. 2 is a widthwise cross sectional view of the electrode array during fabrication showing a carrier wafer after a first layer of a substrate has been disposed atop.

Referring to FIG. 2, the method utilizes a carrier wafer 60. The carrier wafer 60 of the illustrated embodiment comprises silicon (Si). Of course other materials may also be suitable for forming the carrier wafer 60, as realized by those skilled in the art.

The method includes the step of depositing a first composition (not separately numbered) on the carrier wafer 60 as shown in FIG. 2. The first composition forms the first layer 38 described above. The first composition is preferably a non-conductive material and more preferably, the first composition is a polymer. Most preferably, the first composition is Parylene C and is applied by vapor deposition.

Figure 3:
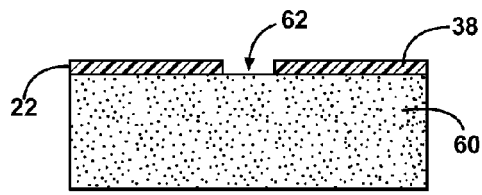
FIG. 3 is a widthwise cross sectional view of the electrode array during fabrication showing a longitudinal slit defined by the first layer.

Referring to FIG. 3, a longitudinal slit 62 is defined in the first layer 38. In the illustrated embodiment, lithography is utilized to demarcate the area of the slit 62 on the first layer 38. Then, the area of the first layer 38 is removed using a directional oxygen ($O_2$) plasma reactive ion etching (RIE) to define the slit 62. Of course, other techniques for defining the slit 62 may be realized by those skilled in the art. In the illustrated embodiment, the longitudinal slit 62 has a length of about 16 mm and a width of about 5-20 µm.

Figure 4:
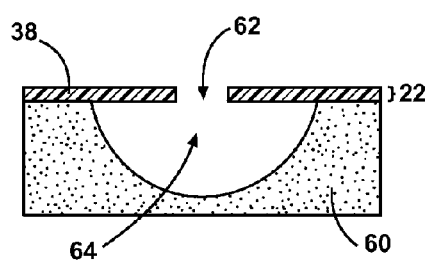
FIG. 4 is a widthwise cross sectional view of the electrode array during fabrication showing a carrier channel defined by the carrier wafer underneath the first layer.
Figure 5:
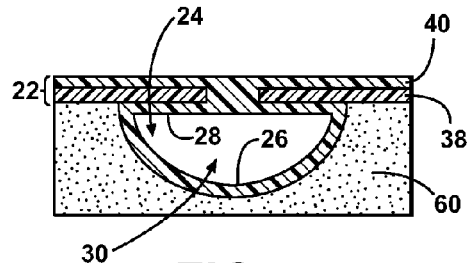
FIG. 5 is a widthwise cross sectional view of the electrode array during fabrication showing a tube and a second layer of the substrate.
Figure 6:
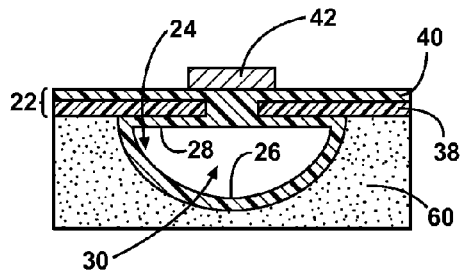
FIG. 6 is a widthwise cross sectional view of the electrode array during fabrication showing a feed line disposed on the second layer.
Figure 7:
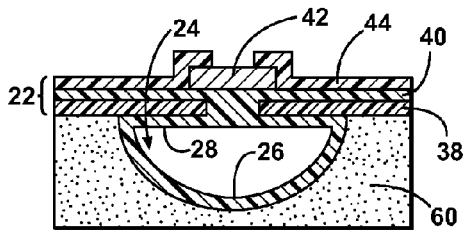
FIG. 7 is a widthwise cross sectional view of the electrode array during fabrication showing a third layer of the substrate disposed on the second layer and the feed line.

The method also includes etching the carrier wafer 60 through the longitudinal slit 62 to define a channel 64 underneath the first layer 38, as shown in FIG. 4. The channel 64 in the carrier wafer 60 is referred to hereafter as the carrier channel 64. In the illustrated embodiment, the etching of the carrier wafer 60 to form the carrier channel 64 is accomplished using xenon difluoride. However, those skilled in the art realize may realize other suitable techniques for generating the carrier channel 64.

In the illustrated embodiment, the maximum depth of the carrier channel 64 is about 150-200 µm below a top level of the substrate 60. Said another way, the depth of the carrier channel 64 is about 150-200 µm below the first layer 38. Of course, other depths may alternatively be generated. The width of the carrier hannel 64 in the illustrated embodiment is about 100-300 µm. The carrier channel 64 may have a generally semicircular cross section, as is shown in FIG. 4. However, those skilled in the art realize that the carrier channel 64 may any of numerous shapes and sizes.

The method further includes the step of depositing a second composition (not separately numbered). The second composition is preferably a non-conductive material and more preferably, the second composition is a polymer. Most preferably, the second composition is Parylene C and is applied by vapor deposition.

In the illustrated embodiment, the second composition is deposited through the longitudinal slit and around the carrier channel 64 to form the tube 24 described above having the tube channel 36. The second composition is also deposited above the first layer 38 to form the second layer 40 described above. Accordingly, the second composition seals the longitudinal slit 62. As such, the tube 24 and second layer 40 are formed of a unitary material in the illustrated embodiment.

The feed lines 42 are disposed on the second layer 40 opposite the tube 24 according to the method. The feed lines 42 are applied to the second layer 40 using evaporated metal and lift off.

The method further includes depositing a third composition (not separately numbered) atop the second layer 40 and the feed lines 42, as shown in FIG. 77. The third composition forms the third layer 44 described above. The third composition is preferably a non-conductive material and more preferably, the third composition is a polymer. Most preferably, the third composition is Parylene C and is applied by vapor deposition. The third layer 44 (as well as the fourth and fifth layers 44, 54) acts as insulation to the feed lines 42. A plurality of apertures 45 are defined in the third layer 44 using directional $O_2$ RIE or other suitable techniques. Each aperture 45 exposes at least one of the feed lines 42.

Figure 8:
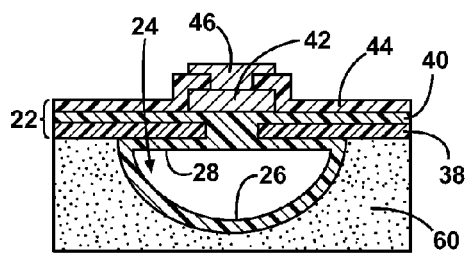
FIG. 8 is a widthwise cross sectional view of the electrode array during fabrication showing an electrode disposed above the third layer and in contact with the feed line.

Referring to FIG. 8, the method continues with the step of disposing a plurality of electrodes 46 on the substrate 22. In the illustrated embodiment, the electrodes are disposed in the apertures 45 such that each electrode 46 electrically connected to at least one of the feed lines 42. Each electrode 46 in the illustrated embodiment is generally circular shaped with a diameter of less than 200 µm. Preferably, each electrode 46 has a diameter of about 180 µm. Of course, other suitable shapes and sizes for the electrodes 46 will be contemplated by those skilled in the art.

In the illustrated embodiment, the electrodes 46 are formed using a lift-off technique. More specifically, photoresist (not shown) is placed on the exposed substrate 22, the photoresist is removed from areas where the electrodes 46 are to be disposed, the Ti—Ir metal (not shown) is disposed on the exposed substrate 22 such that the Ti—Ir metal bonds in the areas where the photoresist has been removed, and acetone (not shown) is applied to the substrate 22. The acetone eats away at the remaining photoresist and removes the Ti—Ir metal, except for the electrodes 46.

Figure 9:
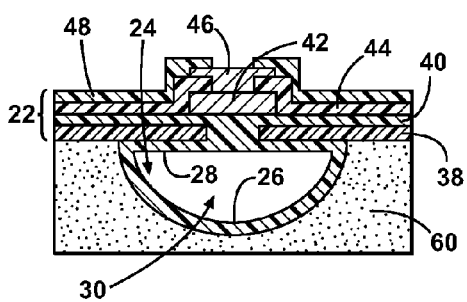
FIG. 9 is a widthwise cross sectional view of the electrode array during fabrication showing a fourth layer of the substrate disposed above the third layer.
Figure 10:
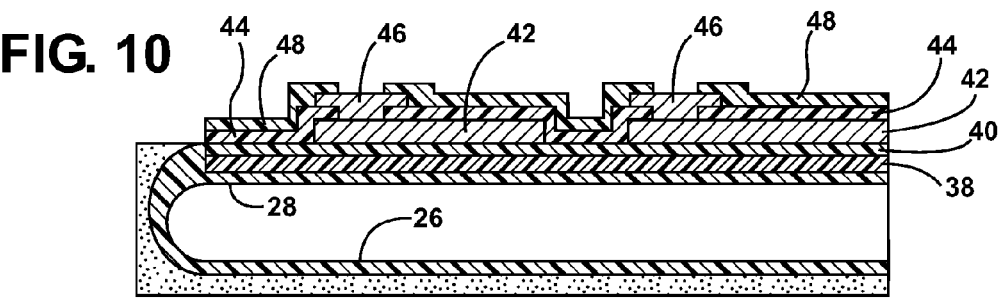
FIG. 10 is a lengthwise cross sectional view of a portion of the electrode array during fabrication showing the fourth layer.

The method also includes the step of depositing a fourth composition (not separately numbered) atop the third layer 40, as shown in FIGS. 9 and 10. The fourth composition forms the fourth layer 48 described above. The fourth composition is preferably a non-conductive material and more preferably, the fourth composition is a polymer. Most preferably, the fourth composition is Parylene C and is applied by vapor deposition.

Figure 11:
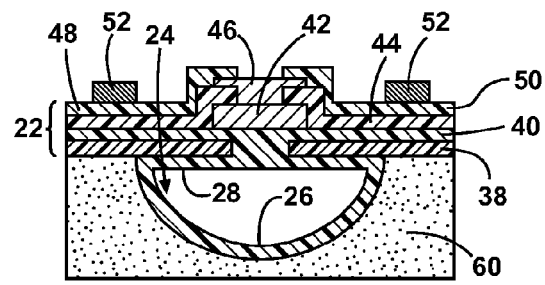
FIG. 11 is a widthwise cross sectional view of the electrode array during fabrication showing a curl strip disposed above the fourth layer.
Figure 12:
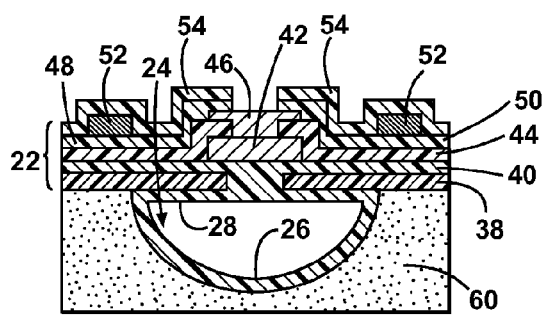
FIG. 12 is a widthwise cross sectional view of the electrode array during fabrication showing a fifth layer of the substrate disposed above the curl strip and the fourth layer.

The method further includes the step of disposing the curl strip 52 on the substrate 22. Preferably, the curl strip 52 is disposed adjacent the peripheral edge 50, as shown in FIGS. 11 and 12. After disposition of the curl strip 52, a fifth composition (not separately numbered) is deposited atop the fourth layer 48 and the curl strip 52. The fifth composition forms the fifth layer 54 described above. The fifth composition is preferably a non-conductive material and more preferably, the fifth composition is a polymer. Most preferably, the fifth composition is Parylene C and is applied by vapor deposition.

The method also includes the step of forming the plurality of openings 56 in the fourth and fifth layers 48, 52 to expose the electrodes 46. The openings 56 are created using directional $O_2$ RIE or other suitable techniques. The openings 56 allow electrical conduction with the electrodes 46. Preferably, one opening 56 is formed for each electrode 46.

The use of five compositions forming five layers 38, 40, 44, 48, 54 is not absolutely necessary in forming the substrate 22 of the electrode array 20. Several of these layers 38, 40, 44, 48, 54 could be combined and/or the compositions applied in combination.

Figure 13:
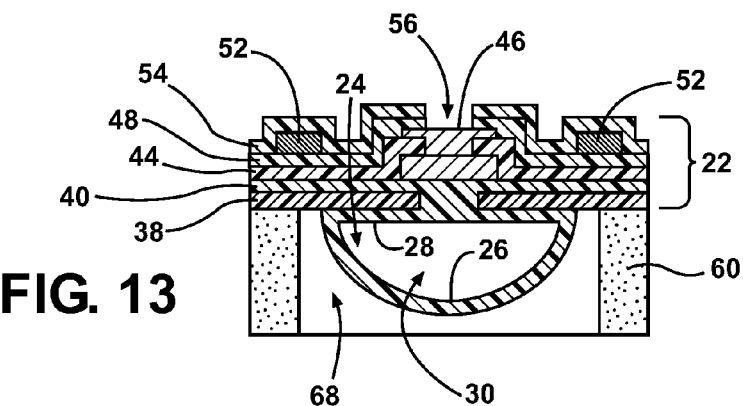
FIG. 13 is a widthwise cross sectional view of the electrode array during fabrication showing a void disposed in the carrier wafer opposite the substrate.
Figure 14:
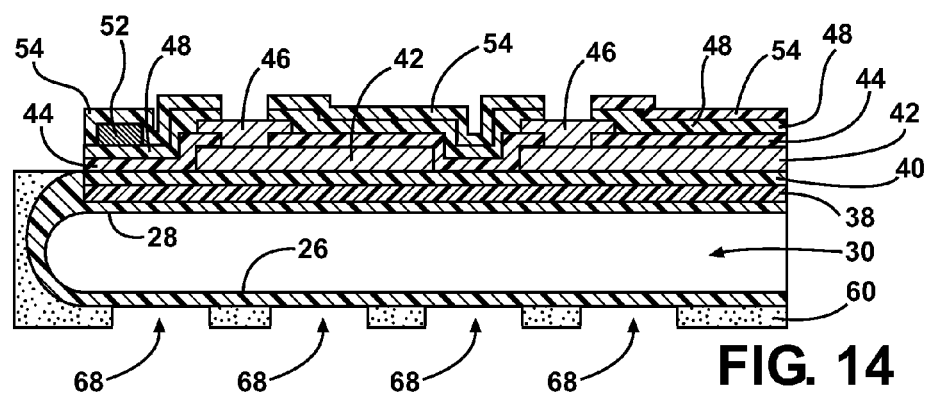
FIG. 14 is a lengthwise cross sectional view of a portion of the electrode array during fabrication showing voids disposed in the carrier wafer opposite the substrate.
Figure 15:
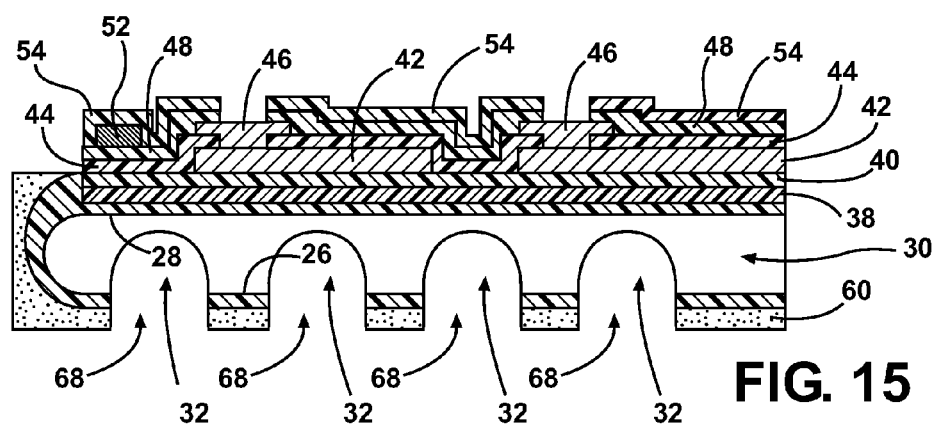
FIG. 15 is a lengthwise cross sectional view of a portion of the electrode array during fabrication showing slots defined by the tube to expose a tube channel.

Referring to FIGS. 13 and 14, the method continues with the step of etching the carrier wafer 60 opposite the substrate 22 to define voids 68 with each void 68 exposing an area (not separately numbered) of the tube 24. The creation of the voids 68 is performed using directional RIE or other suitable techniques.

After the voids 68 have been defined in the carrier wafer 60, the method proceeds with removing the areas of the tube 24 exposed by the voids 68 to define the slots 32 within the tube 24. The slots 32 are generated using oxygen plasma.

The method further includes the step of releasing the tube 24 and substrate 22 from the carrier wafer 60. In the illustrated embodiment, the tube 24 and substrate 22 are released from the carrier wafer 60 by dissolving the carrier wafer 60 using a solution including potassium hydroxide (KOH). Preferably, the solution is about 2% KOH. However, other techniques may be implemented as realized by those skilled in the art.

Figure 17:
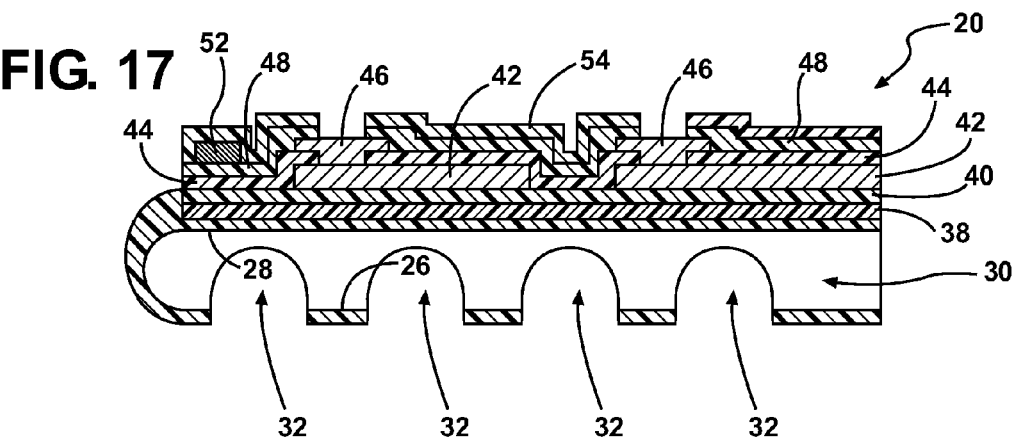
FIG. 17 is a lengthwise cross sectional view of a portion of the electrode array.
Figure 18:
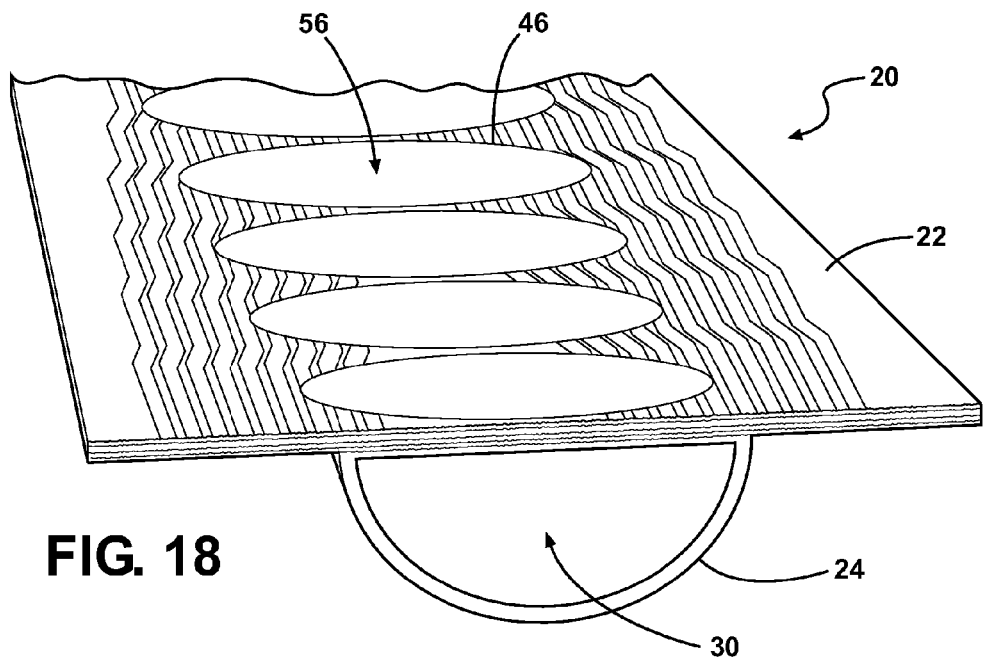
FIG. 18 is a perspective view of a portion of the electrode array.
Figure 19:
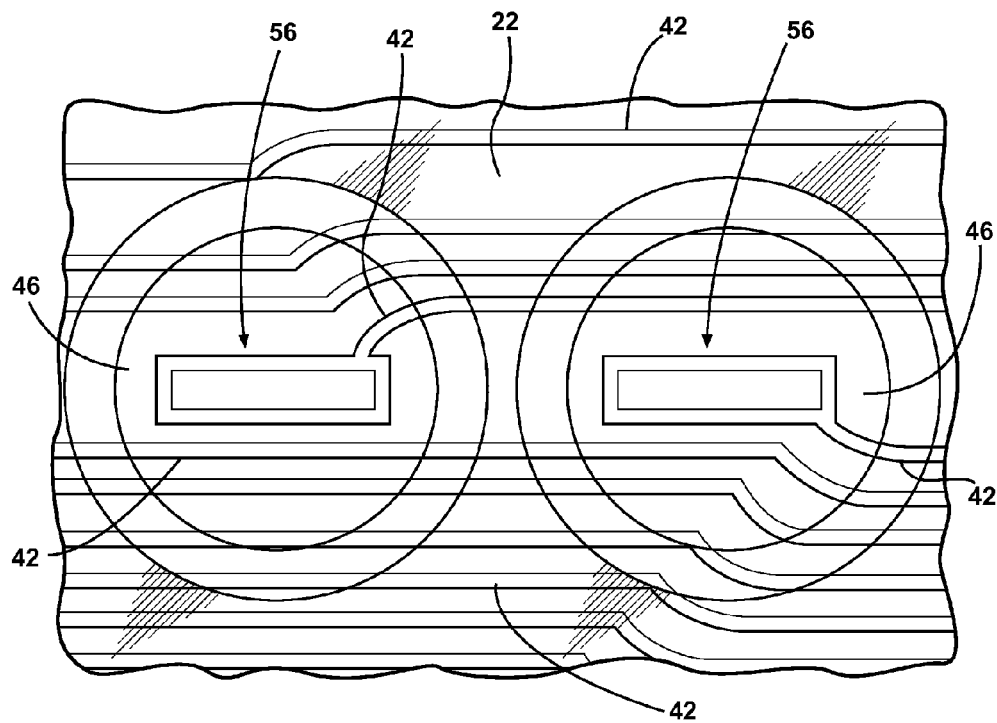
FIG. 19 is a close-up top view of a pair of electrodes of the electrode array.
Figure 20:
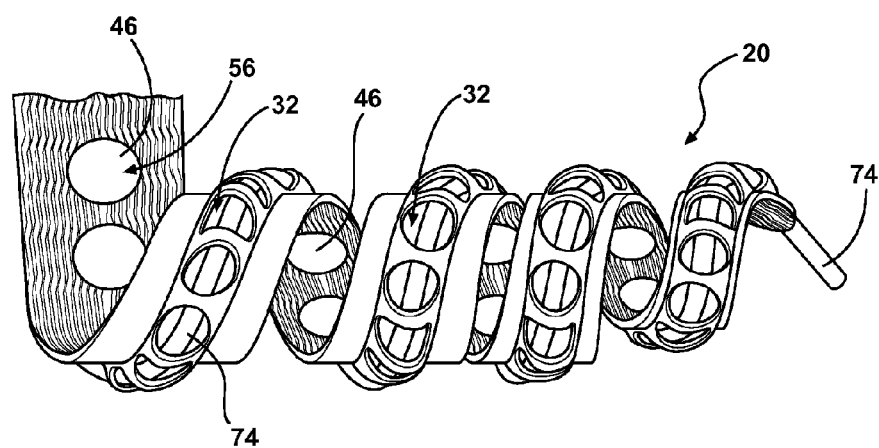
FIG. 20 is a perspective view of a portion of the electrode array with a wire disposed

FIGS. 16 and 17 show cross sectional views of the electrode array 20 after release from the carrier wafer 60. Furthermore, FIG. 18 shows a perspective view of a portion of the electrode array 16 and FIG. 19 shows a close up top view of two electrodes 46 and a plurality of feed lines 42.

Curl may be induced into the electrode array 20 by utilizing a wire 74. The wire 74 is disposed through the tube channel 30 to hold the array 20 in a curled position.

The electrode array 20 provides high electrode 46 density, built in curl, integrated positioning, and tailored stiffness for use as part of the cochlear implant. The substrate 22 is flexible and robust enough to withstand the tight helical pitch of the cochlea. This substrate 22 can hug the modiolus of the cochlear for close proximity to neural receptors. The size and spacing of the openings 56 can be altered to make the array stiff enough for insertion in the cochlea yet pliable enough to curl. The openings 56 also provide a lumen where a stylet wire (not shown) can be advanced to straighten the array for insertion into the cochlea and then fed off the array to allow it to curl into the cochlea. Alternatively, a microelectromechanical systems (MEMS) solution may be implemented to perform insertion of the electrode array 20 into the cochlea.

The electrode array 20 may also find application as part of a neural probe (not shown). Polymer neural probes are of increasing interest because they more closely match the tissue compliance then harder silicon or glass probes. This match in compliance improves the synchronicity of probe motion with that of the tissue, so that the probes do not tear through the tissue in response to micro motions. However, the typical drawback of polymer probes is that they are highly flexible and need to be strengthened with stiffeners in order to penetrate the brain tissue.

The electrode array 20 may also find application with for dispensing cell growth promoters or pharmaceuticals to the surrounding tissue through the tube channel 30, either with or without the slots 32. The tube channel(s) 30 beneath the electrodes 20 may be used to deliver other fluid locally to surrounding cells. Electrochemical reactions can be studied locally, by stimulating cells chemically and recording the electrical response via the electrodes 46. Alternatively or additionally, the electrodes 46 may be used to electrically stimulate cells.

Prior art polymer electrode arrays have been designed with drug delivery channels. However, the channels were fabricated using sacrificial photoresist. The photoresist is sandwiched between two polymer layers such that when it is dissolved away it leaves an empty space (channel) in the polymer. The sacrificial process of the prior art has the drawback of limiting the cross-sectional dimensions of the channel to the maximum thickness the resist can be spun on, typically less than 100 µm. In comparison, the cross-sectional dimensions of the tube channel 30 of the present invention are only limited by the thickness of the carrier wafer 64, thus providing cross-sectional dimensions up to about 500 µm. Furthermore, these cross-sectional dimensions can even be extended beyond that through bonding of carrier wafers 64.

The present invention has been described herein in an illustrative manner, and it is to be understood that the terminology which has been used is intended to be in the nature of words of description rather than of limitation. Obviously, many modifications and variations of the invention are possible in light of the above teachings. The invention may be practiced otherwise than as specifically described within the scope of the appended claims.

What is claimed is:

1. An electrode array comprising:
a tube having at least one wall defining a channel;
a substrate comprised of non-conductive material and supported at least partially by the tube;
a plurality of electrodes comprised of a conductive material and supported by the substrate; and
a plurality of feed lines comprised of a conductive material and disposed primarily within the substrate wherein each feed line is electrically connected to at least one of the plurality of electrodes;
wherein the at least one wall of the tube is continuous to allow liquids to pass through the tube channel defines a plurality of slots into the hollow channel for regulating stiffness and curl of the tube.

2. An electrode array as set forth in claim 1 wherein the tube comprises Parylene.

3. An electrode array as set forth in claim 1 wherein the tube comprises a metal.

4. An electrode array as set forth in claim 1 wherein the substrate defines a peripheral edge and the electrode array further comprises a curl strip disposed adjacent at least a portion of the peripheral edge.

5. An electrode array as set forth in claim 4 wherein the curl strip is bimetallic.

6. An electrode array as set forth in claim 1 wherein the electrodes comprise metal.

7. An electrode array as set forth in claim 1 wherein the substrate includes a first layer of a polymer supported at least partially by the tube and at least one insulating layer of a polymer disposed on the base layer opposite the tube.

8. An electrode array as set forth in claim 7 wherein said at least one insulating layer comprises a second layer disposed on the first layer opposite the tube and a third layer disposed on the second layer opposite the tube.

9. An electrode array as set forth in claim 8 wherein the feed lines are disposed between the first layer and the second layer.

10. An electrode array as set forth in claim 9 wherein the electrodes are disposed between the second layer and the third layer.

11. An electrode array as set forth in claim 1 wherein each of said electrodes has a generally circular shape and a diameter less than 200 μm and a pitch between electrodes of less than 300 μm.

12. An electrode array as set forth in claim 1 wherein the at least one wall of the tube includes one or more slots that regulate the stiffness and curl of the tube.

13. An electrode array as set forth in claim 12 wherein the size of the slots define the ability of the tube to bend and curl.

14. An electrode array as set forth in claim 12 wherein the spacing of the slots relative to one another define the ability of the tube to bend and curl.

15. An electrode array as set forth in claim 12 wherein the size of the slots and the spacing of the slots relative to one another define the ability of the tube to bend and curl.

* * * * *